United States Patent [19]

Saunders

[11] Patent Number: 5,079,029

[45] Date of Patent: Jan. 7, 1992

[54] FINGERPRINT DETECTION

[76] Inventor: George C. Saunders, Rt. 1, Box 428B, Espanola, N. Mex. 87532

[21] Appl. No.: 366,951

[22] Filed: Jun. 16, 1989

[51] Int. Cl.⁵ .............................................. A61B 5/117
[52] U.S. Cl. ........................................ 427/1; 427/145; 427/343
[58] Field of Search ............................ 427/1, 145, 343

[56] References Cited

U.S. PATENT DOCUMENTS

| | | | |
|---|---|---|---|
| 2,986,831 | 6/1961 | Terek et al. | 427/1 |
| 3,075,852 | 1/1963 | Bonora | 427/1 |
| 4,260,645 | 4/1981 | Kerr et al. | 427/1 |
| 4,313,734 | 2/1982 | Leuvering | 23/230 B |
| 4,719,119 | 1/1988 | Thompson et al. | 427/1 |
| 4,752,567 | 6/1988 | De Brabander | 435/7 |

Primary Examiner—Janyce Bell

[57] ABSTRACT

A method for detection and visualization of latent fingerprints is provided and includes contacting a substrate containing a latent print thereon with a colloidal metal composition for time sufficient to allow reaction of said colloidal metal composition with said latent print, and preserving or recording the observable print. Further, the method for detection and visualization of latent fingerprints can include contacting the metal composition-latent print reaction product with a secondary metal-containing solution for time sufficient to allow precipitation of said secondary metal thereby enhancing the visibility of the latent print, and preserving or recording the observable print.

11 Claims, No Drawings

FINGERPRINT DETECTION

This invention is the result of a contract with the Department of Energy (Contract No. W-7405-ENG-36).

FIELD OF THE INVENTION

The present invention relates to the field of latent print detection.

BACKGROUND OF THE INVENTION

Fingerprints are impressions of the system of ridges on the finger surface. Most latent fingerprints, i.e., those hidden from the unaided eye, are formed when perspiration escapes through the ridged surface. Human perspiration is a mixture of many substances including fatty acids, proteins, peptides, amino acids, chloride salts, water, and urea.

Under present forensic science practices, the particular analytical technique used for fingerprint detection varies depending upon the type of substrate. For example, the typical process on a paper substrate involves application of ninhydrin (triketohydrindene hydrate) to the paper and allowing the print to develop by heating under high humidity. Ninhydrin is commonly used as a colourimetric reagent for determination of, e.g., amino acids (see The Condensed Chemical Dictionary, 10the Ed., Van Nostrand Reinhold Co., 1981).

Another process for detecting latent fingerprints on surfaces that have been exposed to water involves the use of a reagent known as physical developer (PD) or stabilized physical developer (SPD). This process uses a silver-based reagent typically including ferrous ammonium sulfate, ferric nitrate, silver nitrate, a citric acid buffer and one or more surfactants. One disadvantage in this process is that the substrate is generally soaked in a maleic acid solution as one step. Maleic acid presents mild handling problems. Another disadvantage is that the process uses a significant amount of silver per application as one batch uses about 20 grams (g) of silver nitrate and is useful for up to about forty runs or about two days. Thus, this process may use from about 0.5 g up to about 20 g of silver nitrate for each potential print depending on the number of runs.

Within the past decade, a process using the fumes of cyanoacrylate esters for the detection of latent fingerprints has also found widespread use on a range of substrates. Such esters are particularly useful on materials such as polystyrene. However, there are some problems with the toxicity of these materials.

Although numerous other fingerprint detection techniques have been developed, extensive research has continued over the past decade in the field of latent print detection. One difficulty has been in developing a technique usable to detect latent fingerprints found on a wide range of potential substrates.

Accordingly, it is an object of this invention to provide a widely usable method or technique for the detection and visualization of latent fingerprints.

SUMMARY OF THE INVENTION

In accordance with the objects and purposes of the present invention, the present invention provides a method for detection and visualization of latent fingerprints comprising contacting a substrate containing a latent print thereon with a colloidal metal composition at a suitable pH, preferably a pH of from about 2.5 to about 4.0, for time sufficient to allow reaction of said colloidal metal composition with said latent print, and preserving or recording the observable print. In a further embodiment of the invention there is provided a method for detection and visualization of latent fingerprints comprising contacting a substrate containing a latent print thereon with a colloidal metal composition at a suitable pH, preferably a pH of from about 2.5 to about 4.0, for time sufficient to allow reaction of said colloidal metal composition with said latent print, further contacting the metal composition-latent print reaction product with a secondary metal-containing solution for time sufficient to allow precipitation of said secondary metal upon the metal composition-latent print reaction product thereby enhancing the visibility of the latent print, and preserving or recording the observable print.

The present invention further provides a method of transferring and developing a latent fingerprint by contacting a latent fingerprint-containing substrate with a transfer medium under sufficient pressure to effect at least a partial transfer of the fingerprint, followed by contacting the latent fingerprint-containing transfer medium with a colloidal metal, e.g., gold, composition at a suitable pH, preferably a pH of from about 2.5 to about 4.0, for time sufficient to allow reaction of said colloidal gold composition with said latent print, and preserving or recording the observable print. Optionally, the gold composition-latent print reaction product upon the transfer medium can be contacted with a secondary metal-containing solution for time sufficient to allow precipitation of said secondary metal upon the gold composition-latent print reaction product thereby enhancing visibility of the latent print prior to preserving or recording the observable print.

The present invention still further provides a fingerprint developing kit including a colloidal gold composition, and a secondary metal containing solution.

DETAILED DESCRIPTION

While colloidal metal particles, e.g., colloidal gold particles, have been widely used in the fields of biochemistry, histology, pharmacology, cytology and immunochemistry as metal labelers (e.g., U.S. Pat. No. 4,313,734 discloses using colloidal metal particles such as colloidal gold particles for immunoassay), the method of the present invention wherein colloidal metal, e.g., gold, compositions are used in the detection and visualization of latent fingerprints has not previously been reported and has been found useful on a surprisingly wide variety of substrates.

In the present process, colloidal metal particles are used to detect and develop fingerprint components, e.g., amino acids, proteins or lipids. By "fingerprints", it is meant throughout this specification to refer as well to footprints and palmprints that also leave characteristic marks. While not wishing to be bound by the present explanation, such a process is believed to involve binding of the colloidal metal particles to such fingerprint components. This can be accomplished either in situ upon a latent fingerprint-containing substrate or on a latent fingerprint transferred from an original substrate surface to a suitable transfer medium, e.g., a transfer membrane. The colloidal metal particles may be metal or metal compounds such as metal oxides or hydroxides. For example, the colloidal metal particles may be gold, silver, platinum, or copper, or similarly may be copper hydrous oxide, iron oxide, iron hydroxide, aluminum oxide, aluminum hydroxide, titanium dioxide and the like. The preferred colloidal metal particles include gold and titanium, with gold being the most preferred as the colloidal metal.

The preparation of colloidal metal particles, in particular gold particles are well known. Further reference may be made to, e.g., Techniques in Immunocytochemistry Vol.—2, Bullock, G. R. and Petrusz, P. (ed.), Academic Press, London, 1983, pp. 217-284; and, U.S. Pat. No. 4,313,734. A particularly useful preparation of a gold sol or colloidal gold composition is described by G. Frens in Nature Physical Science 241, 20 (1973) and involves first boiling a solution of tetrachloroauric acid, adding a solution of trisodium citrate, cooling the resultant colloidal gold solution and optionally adding a surfactant and a buffer such as citric acid.

Colloidal gold particles useful in the practice of this invention are generally from about 5 nanometers (nm) to about 200 nm in diameter. The colloidal gold particles are contained within a suitable gold composition. Such a solution can typically further contain a wetting agent, a dispersant, a detergent, and a suitable buffer. Suitable colloidal gold compositions are easily prepared, but are also commercially available from several companies including, e.g., Janssen Life Sciences Products, Piscataway, N.J. (AuroDye TM forte kit) or Zymed Laboratories Inc., South San Francisco, Calif.

The process of this invention is useful on a wide range of substrates including both rough and smooth surfaces, on both porous and nonporous materials, on wet surfaces, and on both colored and noncolored surfaces. For example, the process is useful, e.g., on a variety of tapes such as masking tapes, strapping tapes, electrical tapes, Teflon TM polyfluorocarbon tapes, adhesive tapes, and athletic or medical tapes, on government issued paper such as treasury checks, on credit cards, on the rough plastic covering of floppy disks, on polystyrene, polypropylene, polyethylene and the like, on metal substrates such as aluminum and the like, and on glass.

After a sufficient incubation or development period, the fingerprint components bound to the colloidal gold particles can be visually observed, if present in sufficient quantity. Generally, on a nonblack background such as a white or light-colored background and even a dark blue background, such developed prints can generally be observed as pinkish- or reddish-colored prints. Otherwise, if an insufficient quantity of an original or transferred latent fingerprint is present whereby there is not an observable print after treatment with the colloidal gold composition, a second metal, e.g., nickel or silver, can be used to enhance or amplify the gold signal. The colloidal gold-latent print reaction product, i.e., the bound gold particles, can provide nuclei around which the secondary metal, e.g., nickel or silver, can precipitate thereby enhancing the visibility of the latent fingerprint.

A secondary metal-containing solution can be used to further develop or enhance the visibility of the gold composition-latent print reaction product. Suitable secondary metals include silver and nickel and such metals may conveniently be present as redox-type solutions of the metal. One advantage of using, e.g., this silver process, rather than the physical developer process of the prior art is that the present process generally requires a far smaller amount of silver, generally less than about 1 g of silver nitrate for any potential print or specimen.

Presoaking of paper, i.e., cellulosic substrates, prior to contacting such substrates with the colloidal metal, e.g., gold, compositions can reduce nonspecific binding or reaction with the colloidal gold particles. Nonspecific binding or reaction may occur between the colloidal gold particles and biological components naturally present within the paper. Presoaking can be conducted in distilled water or other suitable aqueous media.

The technique of transferring a fingerprint from its original location prior to the use of the present process for detecting latent prints involves wetting a suitable transfer medium or print-receptive membrane, e.g., a nitrocellulose membrane, a polyvinylidine fluoride membrane (Immobilon P TM transfer membrane, available from Millipore Corp.), or a nylon membrane, and placing it against the latent print-containing substrate with sufficient pressure to effect transfer of at least a portion of the latent print material. The transfer medium is allowed to dry and then wetted with distilled water containing 1% by volume polyoxyethylene sorbitan prior to contacting the transfer medium with the colloidal metal. In practice, a reverse copy of the latent fingerprint may be transferred to the transfer medium, while a portion of the latent fingerprint remains upon the original substrate.

In the practice of the present invention, the substrate containing the suspected latent fingerprint is contacted with the colloidal metal, e.g., gold, composition for time sufficient to allow reaction of the colloidal gold composition with any lament print, generally from about 30 to 120 minutes. When the substrate is paper or a similar cellulosic type material, the substrate is presoaked in several changes of distilled water to reduce nonspecific binding or reaction of the colloidal metal. After contact with the colloidal metal composition, the substrate is rinsed in several changes of distilled water for from about 1 to about 15 minutes. The substrate is then contacted with a secondary metal-containing solution, generally a silver redox type solution, for time sufficient to enhance the visibility of any latent prints, generally from about 5 to about 15 minutes. The substrate is then rinsed with distilled water and allowed to air dry. Any developed print may then be photographed for subsequent evaluation.

The present invention is more particularly described in the following examples which are intended as illustrative only, since numerous modifications and variations will be apparent to those skilled in the art.

EXAMPLE A

A colloidal gold composition was prepared as follows. To a liter of distilled water was added millimeter (ml) of a 10% by volume solution of tetrachloroauric acid. This solution was heated to boiling, 10 ml of a 1% by volume solution of trisodium citrate was added, and boiling was continued for about 10 minutes. The solution should have changed color from blue to a dark red. A small portion (5 ml) of a surfactant, polyoxyethylene sorbitan (available as Tween TM 20 from J.T. Baker Chemical Co.) was then added. The solution was cooled and sufficient citric acid (about a ml of 0.5 Molar citric acid) was added to adjust the pH of the solution to 3.0.

EXAMPLE B

For a silver-containing solution, a first precursor solution (I) was prepared from 33 g of ferric nitrate, 82 g of ferrous ammonium sulfate, 22 g of citric acid, 1 ml of polyoxyethylene sorbitan, and 1 L of distilled water. A second precursor solution (II) was prepared from 20 g of silver nitrate and 100 ml of distilled water. The second solution should be stored in a dark container at room temperature. The silver-containing solution was prepared just prior to use from the precursor solutions by mixing 99 ml of solution I and 1 ml of solution II.

EXAMPLE 1

U.S. treasury checks were soaked in successive changes of distilled water for 30 minutes. The checks were then placed into the colloidal gold solution from Example A at a pH of 3.2 for 20 minutes. The checks were rinsed in several changes of distilled water for 15 minutes and placed into the silver-containing solution (a modified physical developer solution) from Example B until the latent prints had become well developed, about 10 minutes. The checks were again rinsed in several changes of distilled water for 10 minutes and allowed to air dry. The developed latent prints could be observed upon the treasury checks without significant interference from the paper stock.

EXAMPLE 2

The protective plastic covering of a floppy disk was immersed in a colloidal gold solution (prepared from a AutoDye TM forte kit from Janssen Life Sciences Products) at a pH of 3.0 for 1 hour. The disk was rinsed in a stream of distilled water for one minute. The disk was then placed in a silver enhancing solution (prepared from a IntenSE BL TM kit from Janssen Life Sciences Products) until the latent prints had become well defined, from about 15 to about 50 minutes depending upon the particular colloidal gold solution used. The disk was again rinsed for one minute in distilled water and allowed to air dry. The developed latent prints could be observed upon the floppy disk protective covering.

EXAMPLE 3

A polystyrene container was immersed in the colloidal gold solution from Example A at a pH of 3.0 for 1 hour. The container was rinsed in a stream of distilled water for one minute. The container was then placed in a silver enhancing solution (prepared from a IntenSE BL TM kit from Janssen Life Sciences Products) until the latent prints had become well defined, from about 30 to about 50 minutes. The container was again rinsed for one minute in distilled water and allowed to air dry. The developed latent prints were easily observable upon the polystyrene substrate.

EXAMPLE 4

A fingerprint present on a piece of paper was transferred from the paper to a nitrocellulose membrane by wetting the membrane with distilled water, placing the wetted membrane against the print-containing paper substrate and pressing the wetted membrane against the paper. The nitrocellulose membrane was then processed to reveal the latent fingerprint in the manner of Example 2. The resultant developed latent print was a reverse of the original print.

EXAMPLE 5

Different latent fingerprint containing tapes (shown in Table 1) were tested in a manner similar to the prior examples. Each tape was immersed in the colloidal gold composition for the given time, rinsed with distilled water for a minute, immersed in the silver solution for the given time (sufficient to show development of the print), again rinsed in distilled water for about a minute and air dried. The latent fingerprints on each sample of tape was easily observable after developing of the silver enhancement solution.

TABLE 1

| type of tape | colloidal gold type length of immersion | silver solution type length of immersion |
| --- | --- | --- |
| polyfluorocarbon | type 1 - 60 minutes | type 3 - 60 minutes |
| aluminum | type 2 - 60 minutes | type 4 - 45 minutes |
| masking | type 2 - 30 minutes | type 4 - 30 minutes |
| strapping | type 2 - 30 minutes | type 4 - 30 minutes |
| electrical | type 2 - 30 minutes | type 4 - 30 minutes |
| adhesive | type 2 - 30 minutes | type 4 - 30 minutes |
| yellow plastic | type 2 - 30 minutes | type 4 - 30 minutes | type 1: AuroDye TM forte kit from Janssen Life Science Products
type 2: from Example A
type 3: IntenSE BL TM kit from Janssen Life Science Products
type 4: from Example B

EXAMPLE 6

A plastic weighting boat was immersed in a colloidal titanium dioxide solution at a pH of about 3.0 for several minutes. The boat was removed for the solution nd rinsed with distilled water. The latent print could be observed upon the plastic boat.

Although the present invention has been described with reference to specific details, it is not intended that such details should be regarded as limitations upon the scope of the invention, except as and to the extent that the are included in the accompanying claims.

What is claimed is:

1. A method for detection and visualization of latent fingerprints comprising:
   a. contacting a substrate containing a latent print thereon the a colloidal metal composition at a pH from about 2.5 to about 4.0 for time sufficient to allow reaction of said colloidal metal composition with the latent print; and,
   b. preserving or recording the observable print.

2. The method of claim 1 where the metal composition-latent print reaction product is further contacted with a secondary metal-containing solution for time sufficient to allow precipitation of said secondary metal upon the metal composition-latent print reaction product thereby enhancing the visibility of the latent print.

3. The method of claim 1 wherein the colloidal metal composition is a colloidal gold composition.

4. The method of claim 1 wherein the colloidal metal composition is a colloidal titanium dioxide composition.

5. The method of claim 2 wherein h colloidal metal composition is a colloidal gold composition.

6. The method of claim 5 wherein the secondary metal is silver.

7. A method of transferring and developing a latent fingerprint comprising:
   a. contacting a latent fingerprint-containing substrate with a transfer medium under sufficient pressure to effect at least a partial transfer of the fingerprint;
   b. contacting e latent print-containing transfer medium with a colloidal metal composition at a pH from about 2.5 to about 4.0 for time sufficient to allow reaction of aid collidal metal composition with said latent print; and,
   c. preserving or recording the observable print.

8. The method of claim 7 wherein he metal composition-latent print reaction product is further contacted with a secondary metal-containing solution for time sufficient to allow precipitation of said secondary metal upon the metal composition-latent print reaction product thereby enhancing the visibility of the latent print.

9. The method of claim 7 wherein h colloidal metal composition is a colloidal gold composition.

10. The method of claim 7 wherein the colloidal metal composition is a colloidal titanium dioxide composition.

11. The method of claim 9 wherein the secondary metal is silver.

* * * * *